(12) United States Patent
Purohit et al.

(10) Patent No.: US 7,074,439 B2
(45) Date of Patent: Jul. 11, 2006

(54) PREPARATION OF ESSENTIAL OIL COMPOSITIONS FOR POTABLE LIQUID DISINFECTION

(75) Inventors: Hemant J. Purohit, Nagpur (IN); Manisha Kulkarni, Nagpur (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/833,844

(22) Filed: Apr. 27, 2004

(65) Prior Publication Data

US 2004/0202633 A1    Oct. 14, 2004

Related U.S. Application Data

(62) Division of application No. 10/039,666, filed on Jan. 4, 2002.

(60) Provisional application No. 60/271,678, filed on Feb. 27, 2001.

(51) Int. Cl.
*A01N 65/00*     (2006.01)
*A23L 2/00*      (2006.01)

(52) U.S. Cl. .................. 424/725; 426/66

(58) Field of Classification Search ............... 424/725, 424/742, 404; 426/66; 210/749; 514/937
See application file for complete search history.

(56) References Cited

U.S. PATENT DOCUMENTS

| | | | |
|---|---|---|---|
| 3,975,246 A | | 8/1976 | Eibl et al. |
| 4,239,622 A | | 12/1980 | Ridway |
| 4,966,754 A | * | 10/1990 | Purohit et al. |
| 5,153,229 A | | 10/1992 | Chastain et al. |
| 5,164,416 A | | 11/1992 | Nagai et al. |
| 5,843,375 A | | 12/1998 | Emerson et al. |
| 6,261,460 B1 | | 7/2001 | Benn et al. |
| 6,346,281 B1 | * | 2/2002 | DeAth et al. |
| 6,750,353 B1 | * | 6/2004 | Sorsak |

FOREIGN PATENT DOCUMENTS

| CS | 230352 B | 8/1984 |
|---|---|---|
| DE | 3206851 A | 9/1983 |
| IT | 701572 | 3/1966 |
| WO | WO 97/01348 | 1/1997 |

OTHER PUBLICATIONS http://www.uni-graz.at/~katzer/engl/Ocim_bas.html. Basil (*Ociumum basilicum* L.). Downloaded Oct. 6, 2005.*
http://www.ayurvediccure.com/tulasi.htm. AyurvedicCure.com: Morpheme Tulasi (Holy Basil) Supplements. Downloaded, Oct. 11, 2005.*
http://www.plantnames.unimelb.edu.au/Sorting/Ocimum.html. Multilingual Multiscript Plant Name Data Base: Sorting Ocimum names. Downloaded Oct. 6, 2005.*
http://www.indiamart.com/aayurmed. AayurMed: Biotech Pribated Limited. Downloaded Oct. 6, 2005.*
C.K. Atal and B.M. Kapur, Cultivation and Utilization of Aromatic Plants, Regional Research Laboratory, a Laboratory of Council of Scientific and Industrial Research, 1982, pp. 86, 198-200 and 741.
Bose et al., J. Sci. Ind. Research (1949), 8B: 157-160. Influence of Organic Matter on the Bactericidal Efficiency of Indian Essentials Oils.
http://edicion-micro.usal.es/web/educativo/m_especial/15texto.2htm (Mar. 11, 2003).
Rideal, Samuel. Disinfection and the Preservation of Food (1903), John Wiley and Sons, New York, pp. 451-473.
Lawless, Julia. The Illustrated Encyclopedia of Essential Oils: The Complete Guide to the Use of Oils in Aromatherapy and Herbalism (1995). Element Books Limited, Great Britain, pp. 112, 113, 139-141, 206, 223 and 133.
Beylier, M.F. Pefumer & Flavorist (1979), 4: 23-25. Bacteriostatic Activity of Some Australian Essential Oils.
Kuriata et al. Argric. Biol. Chem. (1982), 46(1): 159-165. Synergistic Antimicrobial Effect of Sodium Chloride and Essential Oil Components.

* cited by examiner

*Primary Examiner*—Michele Flood
(74) *Attorney, Agent, or Firm*—Drinker Biddle & Reath LLP; Daniel A. Monaco

(57) ABSTRACT

The present invention provides compositions comprising an essential oil, methods for preparing the compositions, and methods of disinfecting potable liquid with the compositions.

12 Claims, 1 Drawing Sheet

PREPARATION OF ESSENTIAL OIL COMPOSITIONS FOR POTABLE LIQUID DISINFECTION

CROSS-REFERENCE TO RELATED APPLICATION

This is a divisional of co-pending application Ser. No. 10/039,666, filed Jan. 4, 2002, which claims the benefit of Provisional Application Ser. No. 60/271,678, filed Feb. 27, 2001, the entire disclosure of which is incorporated herein by reference.

FIELD OF THE INVENTION

This invention relates to a simple and natural method for disinfection of potable liquids, such as drinking water, by using a formulation of an essential oil derived from an herbal material. More particularly, this invention relates to a clove oil emulsion preparation, which finds application in disinfection of drinking water contaminated with harmful pathogens to make it potable.

BACKGROUND OF THE INVENTION

Water is life—the concept coined in ancient Indian civilization. The need for pure and safe water is universal. The quest for pure water began in prehistoric times. Criteria of purity have become more complex, more quantitative, perhaps even more rigid, but principles, methods and materials for water purification remained remarkably similar from the earliest recorded data of 2000 BC down to the present time.

The ancient Indian knowledge base on antimicrobial properties of herbs available in nature was the first documented evidence on disinfection. It is true that there were no elaborate tools to establish the validity of these claims. The quest for pure water prompted Rishis to search for suitable herbs in nature and inspired us to check the validity of the concept in modern context. This is the best time to search for such formulation as the whole world is back to nature for simple remedies with no side effects.

In modern times, there are many techniques are available for disinfection of water, and yet rural populations, such as in India, are unable to obtain pure water free from harmful pathogens like *E. coli, Salmonella, Vibrio,* and *Shigella*. These harmful pathogens cause many deadly diseases such as cholera, typhoid, paratyphoid, diarrhea, dysentery, jaundice, shigellosis, etc.

There is thus a need for a simple, inexpensive and widely available purification and disinfecting system for potable liquids, especially water, that is: effective against range of Gram positive and Gram negative bacteria, viruses and other microorganisms; safe and free from the side-effects caused by chemical disinfectants; cost-effective and affordable; simple to use and can be carried anywhere; and requires no special assistance, equipment or training to use.

Essential oils are extensively used medicinally in Ayurveda and Aromatherapy for their great variety of biodynamic actions. Besides antimicrobial and antiseptic properties, they are reported to be antiviral and antitoxic.

Essential oils are used as vital constituents of many cosmetic preparations, as spices, and in medicines. In cosmetics essential oils are mainly responsible for fragrance; in spices, essential oils are the principle ingredients which contribute to the flavor, easy digestibility and (sometimes) to the durability of food.

Essential oils are complex mixtures of odorous, steam volatile or extractable organic compounds, which are synthesized by many types of plants. Typically, the principle constituents of essential oils are aromatic compounds. Essential oils are found various parts of the plant, such as the leaves, stems, flowers, subcuticular space of glandular hairs, in cell organelles, in idioblasts, in excretory cavities, canals, etc. Essential oils may also be found in heartwoods.

Chemically and biogenetically, the natural product class "Essential oils" is heterogeneous. Mono-, sesqui- and diterpenoids (mevalonic acid-derived constituents); phenylpropanoids (cinnamic acid-derived compounds) and alkane derivatives (alkanes, alkenes, alkynes, alkanols, alkanals, alkanoic acids: mostly acetogenins) are by far the most ubiquitous components of essential oils.

Essential oils belong to the so-called "Natural Products" or secondary metabolites of plants. Usually the secondary metabolites are not directly involved in growth and reproduction, but rather in fitness for Life. In other words, secondary metabolites are more involved in the ecology than in the physiology of plants.

Essential oils have long been used as medicines, and are now gaining increased acceptance as aromatic therapies, and as dietary and nutritional supplements. For example, certain names for the clove from India, like "Tikshna-pushpa", "Ruchiram", "Girvana Pushparna" suggest its use as an appetizer, digestive cordial, antitissusive and as mouth freshener. Indications are toothache (local application), indigestion/flatulence, nausea, halitosis and hyperacidity. It is also used as anesthetic and antiseptic in dentistry.

In the doses commonly used for the above-described indications, no adverse reactions have been reported. In a recent study, clove oil used in large doses produced edema, congestion and necrosis (see http://Ayurvedwebline.com).

Essential oils are also widely used in the food industry. For example, clove oil or clove bud oil is used as a compounded oil for the flavoring of pastry, in special sauces and as a condiment. The dried product is used directly in compounded infusions for liqueurs and bitters. The oil is typically used in following proportions:

| | |
|---|---:|
| Non-alcoholic beverages | 3.1 ppm |
| Alcoholic beverages | 300 ppm |
| Ice-cream | 13 ppm |
| Candy | 320 ppm |
| Baked goods | 37 ppm |
| Gelatins and puddings | 0.3–5.0 ppm |
| Chewing gum | 1800 ppm |
| Condiments | 55 ppm |
| Meats | 75 ppm |
| Spiced fruits | 830 ppm |
| Jellies | 7.3 ppm |

Furthermore, clove oil preparations are commonly accepted in the Ayurvedic system, as a safe and accepted medicine.

Antibacterial activity of clove oil has been reported against *V. cholarae*, Gartner's *Bacillus* and Swine *Erysipelas* bacteria and *Brucella* and *Mycobacterium, Trichophyton, Achorion* and *Epidermophyton*. Activity of clove oil volatile fractions is reported by S. Agnihotri and A.D.B. Vaidya against *E. coli, S. aureus, Bacillus subtilis, S. typhi, P. aeruginosa, S. flexneri* and *P. vulgaris*. (See The Wealth of India, Raw Materials, Volume X, p. 93–99, a CSIR publication; World Economic Plants, A standard Reference, 1999, p. 487; and Cultivation and Utilization of Aromatic Plants, edited by C. K. Atal and B. M. Kapur, RRL Jammu Tawi, CSIR Laboratory, 1982, the disclosures of which are herein incorporated by reference).

BRIEF DESCRIPTION OF THE TABLES

Figure 1A:
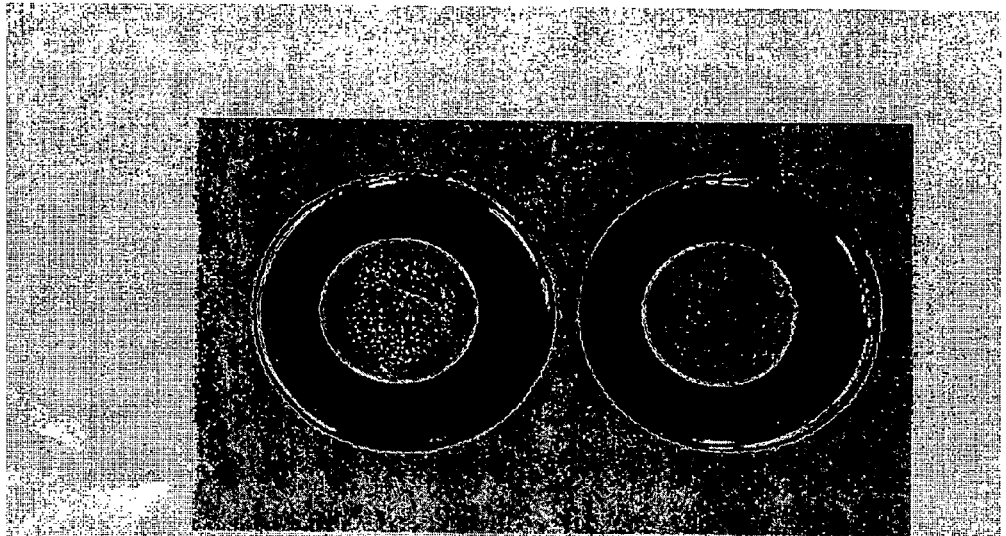
FIG. 1A shows the disinfection activity of a 1:20 dilution of clove oil emulsion E34.

Table 1 depicts the results of essential oil samples screened for antibacterial activity against test organism *E. coli*. The oil samples tested were clove oil, eucalyptus oil, sandal oil, KapurTulsi (*Ocimum kilimandscharicum*) oil and ropan oil in various hydro-alcoholic dilutions by the bore well method.

Table 2 depicts the effect of clove oil on different organisms like *E. coli, Salmonella typhi* and *Vibrio cholarae* in various hydro-alcoholic dilutions.

Table 2A depicts the comparison of activity of clove oil emulsions 1:10, 1:20, 1:30, 1:40 and 1:50 with the standard antibiotics available in the market. The activity was compared by bore well method; zones of inhibition were compared for each emulsion with that of standard antibiotic.

Table 3 displays the results of inhibitory effect of clove oil 1:100 hydro-alcoholic dilutions on log phase and stationary phase cells of *E. coli* by serial dilution method at doses of 100 µl, 50 µl, 25 µl and 12.5 µl.

Table 4 depicts different percentages of detergent Tween®20 in clove oil emulsion preparations. The detergent percentage was varied as 2, 2.5, 3.5 and 4.0%.

Table 5 depicts the different time-periods for which the clove oil emulsion was sonicated (2, 5, 7, 10 and 15 minutes).

Table 6 and Table 7 depict clove oil emulsion preparations with varying percentages of groundnut oil (saturated oil). The different percentages of groundnut oil used were 50, 20, 10, 4, 2, 1 (Table 6) and 0.75, 0.5, 0.2 and 0.1 (table 7) with a sonication time of 2 minutes and 2% of Tween®20.

Table 8 depicts the clove oil emulsions with varying concentrations of unsaturated corn oil. The different percentages were 1.0, 0.75, 0.5, 0.2 and 0.1.

Table 9 depicts preparation of clove oil emulsion with 2% Tween®20 and 0.1% carrier Saffola oil at pH 9.0 at different concentrations of an electrolyte NaCl solution. The concentrations of NaCl used were 0.1 ppm, 0.05 ppm, 0.02 ppm and 0.01 ppm.

Table 10 depicts the preparation of clove oil emulsion using an electrolyte $Na_2HPO_4$ solution in the same conditions and concentration range as stated above for Table 9.

Table 11 depicts the preparation of clove oil emulsion using NaCl solution (0.1 ppm, 0.05 ppm, 0.02 ppm and 0.01 ppm) by diluting the emulsion with pH 9.0 water adjusted by using KOH solution.

Table 12 depicts the preparation of clove oil emulsion using $Na_2HPO_4$ solution (0.1, 0.05, 0.02, 0.02 ppm) by diluting the emulsion with pH 9.0 water that was adjusted to pH 9.0 by using KOH solution.

Table 13 depicts the overall inhibitory effect of clove oil emulsions in sterile drinking water (D.W.) inoculated with *E. coli*.

Table 14 depicts the inhibitory effect of clove oil emulsions prepared using NaCl and $Na_2HPO_4$ after standardizing conditions like emulsifying agent percentage, sonication time, carrier oil percentage and dilutions in water.

Table 15 depicts the percentage removal of *E. coli* by different clove oil emulsions in 1 L spiked water Table 16 depicts the percentage removal of *E. coli* by different clove oil emulsions in 1 L spiked water.

SUMMARY OF THE INVENTION

It has now been found that essential oils may be used as disinfectants for potable liquids, such as water.

The invention provides a composition for the disinfection of a potable liquid, comprising an essential oil; one or more emulsifiers; optionally an electrolyte; and optionally a carrier oil. In one embodiment of the invention, use of carrier oil is preferred, as it substantially favors a stable emulsion preparation. An unsaturated carrier oil, such as Saffola oil (unsaturated corn oil) is preferred.

The invention also provides a method of disinfecting a potable liquid, namely water, comprising providing a composition comprising an essential oil; one or more emulsifiers; optionally an electrolyte; and optionally a carrier oil; and contacting the composition with the potable liquid for a sufficient time to disinfect the potable liquid. As used herein, a "sufficient time to disinfect a potable liquid" means the length of time in which at least about 60%, preferably at least about 80%, more preferably at least about 90% of the microorganisms present in the potable liquid are killed, removed, or growth-inhibited.

As used herein, a "potable liquid" is a liquid intended for consumption by a human being or animal, and includes liquid that may be contaminated with one or more microorganisms.

As used herein, "disinfect" means the killing, removal or inhibition of growth of microorganisms found in a potable liquid.

The invention also provides a method for preparing a composition for the disinfection of potable liquids, comprising making an oil-in-water emulsion of (1) an essential oil; (2) one or more emulsifiers; (3) optionally an electrolyte; and (4) optionally a carrier oil. Preferably, the potable liquid is water.

In one embodiment, the invention provides a composition for disinfecting a potable liquid, said composition comprising a emulsion of an essential oil, emulsifier, optional carrier oil, and electrolyte and water where the emulsion is effective at a concentration at a composition: potable liquid ratio of 1:10000 to 1: 100000.

The invention further provides a composition for disinfecting potable liquid is prepared by mixing the essential oil, emulsifier, optional carrier oil, optional electrolyte and sterile water adjusted to pH range 8.5 to 9.5, to obtain an oil-in-water emulsion. Thus, in one embodiment of the invention, the composition thus prepared has a shelf life of about one year.

In another embodiment, the invention provides a composition for the disinfection of up to 1 L of potable liquid, comprising an essential oil, an emulsifying agent and a carrier oil along with an electrolyte.

In another embodiment of the invention, the composition comprises a clove oil emulsion comprising Tween®20 and Saffola oil with $Na_2HPO_4$ at pH 9.0.

In another embodiment, the composition comprises a clove oil hydro-alcoholic dilutions effective in disinfecting drinking water contaminated with *E. coli, Salmonella typhi* and *Vibrio cholarae*, for example at 1:5000, 1:5000 and 1:100 final dilutions respectively.

DETAILED DESCRIPTION OF THE INVENTION

It has now been found that essential oils may be used as disinfectants for potable liquids, such as water. Potable liquids may be contaminated with any number of harmful microorganisms, including bacteria, viruses, and parasites. It is desirable to remove these microorganisms before humans or animals consume the liquid.

Thus in one aspect, the invention provides a composition for the disinfection of a potable liquid, comprising an essential oil; one or more emulsifiers; optionally an electrolyte; and optionally a carrier oil. The compositions of the invention are useful in removing, killing or inhibiting the growth of various microorganisms in potable liquids, for example in drinking water, thus making the liquid safe for human or animal consumption. For example, the compositions of the invention are useful in disinfecting potable liquids contaminated with fecal coliform bacteria, (e.g., *E. coli*), *Salmonella, Vibrio, Shigella, S. aureus, Bacillus subtilis, S. typhi, P. aeruginosa, S. flexneri* and *P. vulgaris*.

Essential oils are available from a wide variety of plant species. Essential oils are typically mixtures of organic aromatic and other compounds that are extractable from plant material by methods such as steam distillation, cold pressing, $CO_2$ extracted, or extraction with organic solvents (e.g., hexanes), as are known to those of ordinary skill in the art.

Examples of essential oils useful in the present invention include, but are not limited to extracts from Bergamot (*citrus bergamia*); Cedarwood (*cedrus deodara* and *juniperus virginiana*); Cinnamon leaf (*cinnamomum zellanicum* ceylon); Clove or clove bud (*eugenia caryophyllata* madagascar extra; *Syzygium aromaticum* L./*Eugenia aromaticum* L); Eucalyptus (*eucalyptus globulus*& *radiata*); Geranium (*pelargonium graveolens* madagascar bourbon); Grapefruit (*citrus paradisi*); Lavender (*lavendula officinalis* France); (*origanum mariorana*); Patchouli (*pogostemon cablin* E. India dark); Peppermint (*mentha piperita*); Rosemary (*rosmarinus officinalis*); Sandalwood (*aniba rosaeodora*). Other essential oils useful in the present invention include Sandal oil, KapurTulsi (*Ocimum kilimandscharicum*) oil, and Ropan oil. Clove oil (especially from *Syzygium aromaticum* L./*Eugenia aromaticum* L), *eucalyptus* oil and KapurTulsi (*Ocimum kilimandscharicum*) oil are preferred.

A particularly preferred essential oil is clove or clove bud oil from *Syzygium aromaticum* L./*Eugenia aromaticum* L, commonly known as Laung. Clove oil is mainly comprised of eugenol, eugenol acetate and caryophyllene.

Clove bud oil is obtained by water (e.g., steam) distillation of buds in yields ranging from 15–18%. It is a clear, mobile liquid nearly colorless to yellow-brown. It tends to darken on aging. The tinctures, extracts and oleoresins are also useful in the present invention.

As mentioned above, essential oils contain a mixture of chemicals. For example, clove oil contains free eugenol 70–90% ($C_{10}H_{12}O_2$, b.p. 251–254° C.), eugenol acetate 2–17% and caryophyllene ($C_{10}H_{16}O_4$ chiefly the β Form) as main constituents. Both eugenol and eugenol acetate contribute to commercial value of clove oil so the total phenol content is reported as eugenol. Eugenol is widely used in pharmaceutical preparations, in perfumes for soaps and cosmetics and as a flavoring agent in all kinds of foods, meats, sausages and sauces etc. Eugenol acetate is found in nature in clove bud oil and is prepared by acetylation of eugenol. The compound, which is responsible for the characteristic aroma of clove oil, is methyl-n-amyl ketone.

The structure of eugenol is given below:

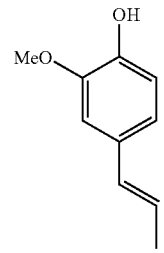

Other common chemical constituents of essential oils are citral (geranial and neral isomers), limonene, linalyl acetate and estragole (methyl chavicol), mono-, sesqui- and diterpenoids (mevalonic acid-derived constituents); phenylpropanoids (cinnamic acid-derived compounds) and alkane derivatives (alkanes, alkenes, alkynes, alkanols, alkanals, alkanoic acids: mostly acetogenins). It is understood that the term "essential oil" as used herein includes the naturally occurring extractable plant oils, mixtures thereof, or one or more of the components found in extractable plant oils, whether naturally or artificially synthesized. The term also includes derivatives and analogs of the components found in extractable plant oils.

The compositions of the invention comprise an emulsifier or surfactant that allows the formation of oil-in-water emulsions and that are regarded as safe for human consumption at the concentrations used in the invention. The terms "emulsifier" and "surfactant" are used interchangeably throughout the specification.

Any suitable emulsifier may be used, for example the Tween®, Myrj™ and Bryj™ surfactants, poloxamers and their derivatives, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, and emulsifying wax. The Tween®surfactants, in particular Tweeng20, are preferred.

The emulsifier may be present in any concentration sufficient to allow formation of a stable oil-in-water emulsion from the essential oil and optional carrier oil. For example, the amount of emulsifier may be from 0.5 to 10%, preferably from 2 to 4% (w/w) of essential oil in the composition. Preferred is a composition comprising 2% Tween®20.

The compositions of the invention may optionally comprise a carrier oil. In some instances, carrier oils allow the formation of finer and more stable emulsions than may be achievable with the essential oil alone. Suitable carrier oils include vegetable and other plant oils; for example Sweet Almond Oil (*Prunus amygdalus* var. *dulcis*); Apricot Kernel Oil (*Prunus armeniaca*); Avocado Oil (*Persea americana*); Black Currant (*Ribes nigrum*); Borage Seed Oil (*Borago officinalis*); Canola Oil (*Brassica napus/campestris*); Rapeseed Oil; Castor Oil (*Ricinus commonus*); Coconut, Copra (*Cocos nucifera*); Corn Oil (*Zea mays*) Evening Primrose Oil (*Oenothera biennis*); Flax Seed Oil (*Linum usitatissimum*); Foraha Oil (*Calophyllum*) (*Calophyllum inophyllum*); Grapeseed Oil (*Vitis vinifera*); Hazelnut Oil (*Corylus Avellana*); Kikui Nut (*Aleurites moluccana*); Macadamia Nut Oil (*Macadami integrifolia, tetraphylla*, or *ternifolia*); Olive Oil (*Olea europaea*); Peanut Oil (*Arachis hypogeae*);

Rose Hip Seed Oil (*Rosa Mosqueta, R. Rubignosa, R. rubirosa*); Safflower Oil (*Carthamus tinctorius*); Sesame Oil (*Sesamum indicum*); Soya Bean Oil (*Glycine max, G. soya*); Sunflower Oil (*Helianthus annuus*); wheat germ oil, kardi oil, sun flower oil or mixtures thereof. The carrier oil may be saturated, unsaturated, or a mixture of saturated and unsaturated oils. Preferred are unsaturated oils, such as Saffola (unsaturated corn oil), kardi oil and sun flower oil, and saturated oils such as groundnut oil.

Suitable amounts of carrier oil for use in the compositions of the invention may be determined by one of ordinary skill in the art, for example by testing the composition according to the procedures outlined in the General Methodologies below. For example, the composition of the invention may comprise carrier oil in the range of about 0.01 to 50% (w/w) of the composition, preferably from 2 and 20% or from about 0.1 to 1%. Particularly preferred are a carrier oil concentrations of 0.1, 0.25, 0.5, 0.75, 1 and 5.0%, for example Saffola oil at 0.1%.

The compositions of the invention may optionally comprise an electrolyte. Suitable electrolytes include NaCl and $Na_2HPO_4$, with $Na_2HPO_4$ as the preferred electrolyte. Other electrolytes are contemplated. Suitable electrolyte concentrations may be determined by one of ordinary skill in the art, by testing compositions according to the procedures outlined in the General Methodologies below.

In preferred compositions, the electrolyte is present in the composition in the range from 0.01 ppm to 0.1 ppm. A preferred electrolyte concentration in the compositions of the invention is 0.1 ppm, for example 0.1 ppm of $Na_2HPO_4$.

The pH of the compositions of the invention may be any pH at which the essential oil emulsion retains its disinfection activity. One of ordinary skill in the art may ascertain appropriate pH's by testing compositions under the procedures outlined in the General Methodologies below. The pH of the compositions of the invention may range, for example, from about 6.0 to about 10, preferably from about 8.5 to about 9.5. Higher or lower pH's are contemplated.

The compositions of the invention may be used to disinfect potable liquids without first being diluted, or may be diluted before use. For example, dilutions of 1:10, 1:100, 1:500 or 1:5000 (with respect to the original emulsion concentration) may be used. Other dilutions are contemplated. One of ordinary skill in the art may ascertain appropriate dilutions by testing compositions under the procedures outlined in the General Methodologies below.

For example, the amount of emulsion used for disinfecting the potable liquid may be in the ratio 1:1,000 to 1:200,000, preferable from about 1:10,000 to 1:100,000 with respect to the final volume of the potable liquid to be disinfected.

In another aspect, the invention provides a method of disinfecting a potable liquid, comprising providing one or more compositions of the invention (or dilutions thereof, as described above) and contacting the composition with the potable liquid for a sufficient time to disinfect the potable liquid. As used herein, a "sufficient time to disinfect a potable liquid" means the length of time in which at least about 60%, preferably at least about 80%, more preferably at least about 90% of the microorganisms present in the potable liquid are killed, removed, or growth-inhibited. One of ordinary skill may determine what is a sufficient length of time for contacting the composition with the potable liquid by testing the potable liquid according to the procedures outlined in the General Methodologies below. For example, the compositions of the invention may be contacted with the potable liquid to be disinfected for about 3 to about 24 hours, preferably from about 6 to about 8 hours, particularly preferably for about 6 hours.

In a further aspect, the invention provides a method for preparing a composition for the disinfection of potable liquids as described above, comprising making an oil-in-water emulsion of (1) an essential oil; (2) one or more emulsifiers; (3) optionally an electrolyte; and (4) optionally a carrier oil. Any suitable method for forming the emulsions may be used, as are familiar to those of ordinary skill in the art; for example, sonicating, shaking, stirring, etc. Preferably, the compositions are prepared by sonication. In particular preferred embodiments, sonication time of about 2 minutes at each step is suitable.

The invention will be illustrated with the following non-limiting examples.

EXAMPLES

General Methodologies

The general methodology adopted for the preparation of inocula of the test bacteria, *E. coli* and the antibacterial assay methods mainly "bore-well" and serial dilution methods are explained below as used in the present invention. Also explained herewith is the procedure for the preparation of essential oil emulsions according to the invention; and the testing and detection methods of the water samples after disinfection. The present invention in its most preferred aspect is the clove oil emulsion preparation comprising the desired proportion of edible detergent, carrier oil and the electrolyte solution with application in disinfection of drinking water.

In preparation of inocula for culturing *E. coli*, Luria-Bertani (LB, HiMedia) media was used. An overnight culture of *E. coli* was grown in LB at 37° C. at 150 rpm and was diluted to five times by LB; the diluted culture was incubated in the same conditions until the optical density (OD) reached 0.5.

Various compositions of essential oils (described below) were screened for antibacterial activity by two methods; viz. bore-well method and serial dilution method.

In the bore-well method, a 1% culture of *E. coli* from log phase was inoculated into molten LB Agar growth medium, and plates were poured. This gave final cell density of about $10^9$ cells per ml. After solidification of the medium, wells were made in the plate with the sterile borer. 100 μl of each essential oil composition was placed in the wells. The plates were incubated at 37° C. overnight. 50% ethanol was placed in the control wells. The plate showed clear zone of inhibition surrounding the wells where there was inhibition of the growth of *E. coli*, confirming the antibacterial effect.

In serial dilution method, *E. coli* culture in log phase growth was diluted in LB broth to $10^3$ cells/ml. One ml of this was taken in each tube, except the first tube in which 2 ml was taken. 100 μl of the essential oil compositions were added to the first tube. One ml from the first tube was transferred to the second and similarly diluted into all the tubes so that each tube contained half the concentration of the composition than the previous tube. Five dilutions were likewise made. The last tube showing no turbidity; i.e., growth in the tube was taken as the Minimum Inhibitory Concentration (MIC) of the composition.

The common acceptance of clove oil by the general population, its safety as well as the potency to kill the gram positive and gram negative bacteria makes the clove oil preferred antibacterial agent for water disinfection.

The essential oils are not soluble in water and oil floats on the surface of water layer. To make the clove oil miscible in water for its uniform dispersion throughout water, oil-in-water type emulsions were prepared by using emulsifying agent, edible grade detergent.

Commercially available I.P. grade clove oil, manufactured by Dabur India Ltd., was used in all the experiments. Five ml packages were procured for the experiments; for every emulsion preparation 5 ml constant volume was used.

To prepare the emulsion, clove oil I.P. 5 ml setting was mixed with 2% Tween®20 (100 µl) and 0.1% Saffola oil (5 µl), sonicated for 2 mins between 2 and 3 of the sonicator (Cole-Parmer, Torbeo, Ultrasonic Processor, 36800 Series) and diluted with sterile distilled water to different dilutions as shown in Table 13.

For better micelle preparation and subsequently stable emulsion it was believed that at pH 9.0 of clove oil emulsion the molecule of eugenol will be in ionized form. With very low concentration of electrolyte NaCl or $Na_2HPO_4$ solution along with 2% Tween®20 and carrier oil 0.1% Saffola oil forms better micelle. In these emulsions, the mixture of clove oil, Tween®20 and Saffola oil was first sonicated as above, diluted 1:10 by sterile distilled water, and the pH of the milky emulsion was adjusted to 9.0 by KOH solution. The concentrations of NaCl used were 0.1 ppm, 0.05 ppm, 0.02 ppm and 0.01 ppm The method was then modified so that instead of changing the pH of diluted emulsion, dilutions were made by pH 9.0 water. For 0.1, 0.05, 0.02 and 0.01 ppm each of NaCl and $Na_2HPO_4$ solution appropriate volumes were taken from 10 ppm stocks and sonicated for 2 minutes again.

As can be seen from the results in Table 13 and 14, the inhibitory effect of emulsions was substantially enhanced with the use of low concentration of electrolytes at pH 9.0.

To test the effect of the emulsions in contaminated water, 1 ml, 100 ml and 1 L volumes drinking water was sterilized by autoclaving and inoculated with *E. coli*. The cell concentrations used were: $10^3$ cells/ml for 1 ml; $10^4$ cells/100 ml for 100 ml; and $10^5$ cells/L for 1 liter.

As specified-above, 2 ml *E. coli* culture in log phase growth at 0.5 OD was centrifuged and the pellet suspended in 1 ml of sterile distilled water in an Eppendorf tube by vortexing to give $10^9$ cells/ml. From this appropriate dilutions were made in sterile distilled water to obtain $10^5$ cells/ml (for 100 ml experiments) and $10^6$ cells/ml for (1 L experiments). 100 µl of the appropriate dilution was used for each flask to get final concentrations of $10^4$ cells/100 ml and $10^5$ cells/L, respectively.

Disinfection activity was assayed by adding an aliquot from the reaction mixture in 2×LB medium after a contact period of 3 hrs, and incubating the LB tubes at 37° C. at 15 rpm overnight. The tubes were then checked for the presence of *E. coli* growth.

Disinfection activity was also assayed by the "Membrane Filter Technique", in which 100 ml of the reaction volume was filtered through sterile membrane filters (Millipore, size 0.45 µm) and the filter discs were placed on MEC agar (Hi-media) plates. The plates were kept at 44.5° C. overnight, the colonies were treated with urea substrate for 15 minutes and the yellow-brown colonies were counted. (See Standard Methods of Water and Waste water Analysis, 17th edition, Section 9213D the disclosure of which is herein incorporated by reference.)

Example 1

Essential oil compositions were screened for antibacterial activity against the test organism *E. coli* (Table 1). Clove oil, eucalyptus oil, sandal oil, KapurTulsi (*Ocimum kilimandscharicum*) oil, and Ropan oil compositions were tested by bore well method as described earlier. Clove oil showed very good disinfection activity against the *E. coli* (Photograph 1) at all dilutions. Eucalyptus oil showed activity in a neat sample, KapurTulsi (*Ocimum kilimandscharicum*) oil showed activity up to a 1:10 dilution, while other compositions showed no activity in hydro-alcoholic dilutions against *E. coli*.

TABLE 1

Essential oil samples tested for antibacteria activity against test organism *E. coli*

| | Effective Dose (HA dilution) | | | | |
|---|---|---|---|---|---|
| Oil Sample | Neat | 1:10 | 1:100 | 1:200 | 1:500 |
| Clove Oil | + | + | + | + | + |
| Eucalyptus oil | + | − | − | − | − |
| KapurTulsi oil | + | + | − | − | − |
| Sandal oil | − | − | − | − | − |
| Neem oil | − | − | − | − | − |
| Ropan oil | − | − | − | − | − |

Example 2

Clove oil hydro-alcoholic dilutions were tested against *Salmonella typhi* and *Vibrio cholarae* along with *E. coli*, at different doses by the serial dilution method. Clove oil was found to inhibit *E. coli* and *Salmonella typhi* growth at all dilutions, while *Vibrio cholarae* growth was inhibited up to dilutions of 1:200 (see Table 2).

TABLE 2

Effect of Clove oil hydro-alcoholic dilutions against *E. coli*, *S. typhi* and *V. cholarae*

| | Effective Dose (HA dilution) | | | | | | |
|---|---|---|---|---|---|---|---|
| Organism | Neat | 1:10 | 1:100 | 1:200 | 1:500 | 1:2000 | 1:5000 |
| *E. coli* | + | + | + | + | + | + | + |
| *Salmonella typhi* | + | + | + | + | + | + | + |
| *Vibrio cholarae* | + | + | + | − | − | − | − |

Example 3

The activity of clove oil emulsions 1:10 (10%), 1:20 (5%), 1:30 (3.33%), 1:40 (2.5%) and 1:50 (2%) was compared with the standard antibiotics available in the market. The activity was compared by the bore well method as described in the General Methodologies above, using 100 µl of each emulsion. Zones of inhibition were compared for each emulsion with that of standard antibiotic and reported Table 2A.

TABLE 2A

Comparison of inhibitory activity of clove oil emulsions with the standard antibiotics available in the market against *E. coli*.

| | Zone of Inhibition (in mm) | | | | | |
|---|---|---|---|---|---|---|
| | | Clove oil emulsion | | | | |
| Antibiotic | Antibiotic | 1:10 | 1:20 | 1:30 | 1:40 | 1:50 |
| Penicillin G | — | 16 | 14 | 12 | 10 | 8 |
| Erythromycin | 10 | 16 | 14 | 12 | 10 | 10 |
| Ampicillin | 14 | 16 | 14 | 12 | 10 | 10 |

TABLE 2A-continued

Comparison of inhibitory activity of clove oil
emulsions with the standard antibiotics
available in the market against *E. coli.*

| | Zone of Inhibition (in mm) | | | | | |
|---|---|---|---|---|---|---|
| | | Clove oil emulsion | | | | |
| Antibiotic | Antibiotic | 1:10 | 1:20 | 1:30 | 1:40 | 1:50 |
| Tetracycline | 24 | 16 | 14 | 12 | 10 | 9 |
| Gentamycin | 24 | 16 | 14 | 12 | 11 | 10 |
| Kanamycin | 30 | 16 | 14 | 12 | 10 | 10 |
| Chloromphenicol | 35 | 18 | 14 | 12 | 11 | 8 |

Example 4

As the bacterial cells in drinking water will essentially be in stationary phase, the experiments were performed to test if there was a different inhibitory dose requirement for log phase as opposed to stationary phase cells. The experiment was carried out by serial dilution method. It was observed that the dose required for both types of cells is the same, as shown in Table 3.

TABLE 3

Effect of Clove oil 1:100 hydro-alcoholic dilutions
on log phase and stationary phase cells

| *E. coli* | Control | 100 µl | 50 µl | 25 µl | 12.5 µl |
|---|---|---|---|---|---|
| Log phase cells | − | + | + | − | − |
| Stationary phase cells | − | + | + | − | − |

Example 5

Five emulsions containing different percentages of Tween®20 (E1 to E5; see Table 4) were made and tested at different dilutions for the ability to disinfect 1 ml, 100 ml, or 1 L of drinking water (D.W.) inoculated with *E. coli* (see General Methodologies, above).

After a 6 hr. contact period, 1 ml of each sample was transferred to a 2×LB tube and monitored for growth as described in the General Methodologies above. Disinfection activity of the diluted emulsions is given in Table 13.

TABLE 4

Clove Oil Emulsions with Different percentages of Tween 20

| Emulsion | Emulsion | | | | |
|---|---|---|---|---|---|
| Constituents | E1 | E2 | E3 | E4 | E5 |
| Clove Oil neat | 5 ml | 5 ml | 5 ml | 5 ml | 5 ml |
| Tween 20 Percentage | 2 | 2.5 | 3.0 | 3.5 | 4.0 |

Emulsion E5 was also tested by varying the number of *E. coli* in the reaction volume ($10^3$ cells, $2\times10^3$ cells and $10^4$ cells) with negative results.

Example 6

The dilutions of emulsion E2 1:10, 1:100 and 1:500 with 2.5% Tween®20 showed positive results in 1 ml while in 1 L reaction volume at the doses of 100 µl, 500 µl and 1 ml gave negative results after contact period of 3 hrs and 6 hrs.

Similarly the emulsions E3 and E4 dilutions showed inhibition of *E. coli* in 1 ml volume and showed negative results when tested in IL water as shown in Table 13.

The emulsion E5 dilutions 1:10, 1:100, 1:500 and 1:5000 with 4% Tween 20 were tested in 1 ml, 100 ml and 1 L volumes displayed positive results in 1 ml at 100 µl and in 1 L at 100 µl 500 µl and 1 ml displayed negative results as shown in Table 13. Emulsions E5 were also tested by varying the cell number of *E. coli* in the reaction volume to $10^3$ cells, $2\times10^3$ cells and $10^4$ cells with negative results.

Example 7

Emulsions E6 to E10 were prepared by changing the sonication time (see Table 5). The emulsions were tested in 100 ml D.W. at a 1:20 dilution test the effect of different sonication times on the disinfection activity of the emulsions. As shown in Table 13, there was no difference in the inhibitory effect with higher sonication time; therefore sonication time of 2 minutes at every step was thought to be sufficient for emulsion preparation.

TABLE 5

Different sonication times in Clove Emulsion Preparation

| Emulsion | Emulsion | | | | |
|---|---|---|---|---|---|
| Constituents | E6 | E7 | E8 | E9 | E10 |
| Tween ® 20 Percentage | 2 | 2.5 | 3.0 | 3.5 | 4.0 |
| Sonication Time | 2 | 5 | 7 | 10 | 15 |

Example 8

Emulsions E11–E15 (Table 6) with 2% Tween®20 and different percentages of groundnut oil were tested for the disinfection activity in 100 ml. Disinfection activity of E12 was observed, but was non-reproducible, so "−" activity is indicated in Table 13 for this emulsion.

TABLE 6

Clove oil emulsion with varying concentrations
of groundnut oil (saturated oil)

| Emulsion | Stock Emulsion | | | | |
|---|---|---|---|---|---|
| Constituents | E11 | E12 | E13 | E14 | E15 |
| Clove Oil neat | 5 ml | 5 ml | 5 ml | 5 ml | 5 ml |
| Tween ® 20 (2%) | 100 µl | 100 µl | 100 µl | 100 µl | 100 µl |
| Groundnut Oil | 250 µl 5% | 200 µl 4% | 150 µl 3% | 100 µl 2% | 50 µl 1% |

Disinfection activity of emulsions E11–E15 is shown in Table 13. Note that in 1 L volume negative results were observed for these emulsions even at 2 ml dose of emulsions E16–E20 with groundnut oil concentrations below 1%

(Table 7) when tested in the 100 ml reaction volume yielded positive effect at the doses of 50 µl and 500 µl after 6 hrs contact period.

TABLE 7

Clove oil emulsion with varying concentrations of groundnut oil (saturated oil)

| Emulsion Constituents | Stock Emulsion | | | | |
|---|---|---|---|---|---|
| | E16 | E17 | E18 | E19 | E20 |
| Clove Oil neat | 5 ml | 5 ml | 5 ml | 5 ml | 5 ml |
| Tween ® 20 (2%) | 100 µl | 100 µl | 100 µl | 100 µl | 100 µl |
| Groundnut Oil | 50 µl 1% | 33.5 µl 0.75% | 25 µl 0.5% | 12.5 µl 0.25% | 5 µl 0.1% |

These results suggest that a lower percentage of carrier oil substantially enhanced the stability and activity of the emulsion, while too high a percentage of carrier oil facilitates the growth of bacteria.

Example 9

Clove oil emulsion E20 (see Table 7) with 2% Tween®20, sonication time of 2 minutes, and 0.1% groundnut oil were diluted 1:20 and tested in 100 ml water with $10^4$ cells of *E. coli* with an overnight contact time. These emulsions showed positive results by 2×LB method and the Membrane Filter Technique. As described above, the filter discs with the filtered samples were placed on MEC agar plates at 44.5° C. overnight and the yellow colonies counted. In 100 ml reaction volume, E20 at the doses of 50 µl, 100 µl, 200 µl and 500 µl gave positive results (Table 13).

Example 10

Emulsions with 0.1% Saffola oil were found to be more fine and stable as compared to the groundnut oil, so the emulsions with 0.1% Saffola oil are preferred.

Emulsion E21 with 0.1% unsaturated, Saffola oil (Table 8) displayed good disinfection activity results in 1 ml volume as shown in Table 13. In 100 ml reaction volume E21 yielded positive activity at doses of 50 µl and 100 µl while in 1 L reaction volume 500 µl and 1 ml dilutions of 1:10 completely inhibited *E. coli* after 6 hrs contact period. Other dilutions were also effective to large extent.

TABLE 8

Clove oil emulsion with Saffola oil (unsaturated corn oil)

| Emulsion Constituents | Stock Emulsion E21 |
|---|---|
| Clove Oil neat | 5 ml |
| Tween ® 20 (2%) | 100 µl |
| Saffola oil | 5 µl, 0.1% |

Example 11

Clove oil emulsions E22–E26 were prepared using an electrolyte NaCl solution, along with 2% Tween®20 and 0.1% carrier Saffola oil at pH 9.0. Concentrations of NaCl used were 0.1 ppm, 0.05 ppm, 0.02 ppm and 0.01 ppm (Table 9). Disinfection activities of emulsions E-22–E-26 are shown in Table 13.

TABLE 9

Preparation of Clove oil emulsion using NaCl solution

| Emulsion Constituents | Stock Emulsion | | | |
|---|---|---|---|---|
| | E22 | E23 | E24 | E25 |
| Clove Oil neat | 5 ml | 5 ml | 5 ml | 5 ml |
| Tween ® 20 (2%) | 100 µl | 100 µl | 100 µl | 100 µl |
| Saffola oil 0.1% | 5 µl | 5 µl | 5 µl | 5 µl |
| NaCl sol'n (10 ppm stock) | 0.1 ppm | 0.05 ppm | 0.02 ppm | 0.01 ppm |

Example 12

Clove oil emulsions E26–E29 were prepared using an electrolyte $Na_2HPO_4$ solution (0.1 ppm, 0.05 ppm, 0.02 ppm and 0.01 ppm) (Table 10). Disinfection activity of these emulsions are shown in Table 13.

It was observed that the better emulsions were obtained when using $Na_2HPO_4$ solution rather than NaCl. Antibacterial effect was substantially enhanced in 0.1 and 0.05 ppm of the electrolyte than the lower concentrations.

The 0.1 ppm $Na_2HPO_4$ solution in the clove oil emulsion at pH 9.0 is the desired electrolyte for the stable and effective emulsion preparation.

TABLE 10

Preparation of Clove oil emulsion using $Na_2HPO_4$ solution

| Emulsion Constituents | Stock Emulsion | | | |
|---|---|---|---|---|
| | E26 | E27 | E28 | E29 |
| Clove Oil neat | 5 ml | 5 ml | 5 ml | 5 ml |
| Tween ® 20 (2%) | 100 µl | 100 µl | 100 µl | 100 µl |
| Saffola oil 0.1% | 5 µl | 5 µl | 5 µl | 5 µl |
| $Na_2HPO_4$ sol'n | 0.1 ppm | 0.05 ppm | 0.02 ppm | 0.01 ppm |

Example 13

Clove oil emulsions E30–E33 were prepared using 0.1 ppm NaCl solution by diluting the emulsion with pH 9.0 water instead of adjusting the pH of diluted emulsion (Table 11). These emulsions were tested for their disinfecting effect. The emulsions at a 1:10 dilution were observed to disinfect 100 ml and 1 L D.W. water after 6 hrs contact period as shown in Table 13.

Similar results were observed in 1:20, 1:50 and 1:100 dilutions of these emulsions, which inhibit growth above 90% of the *E. coli* cells in the given contact period.

TABLE 11

Preparation of Clove oil emulsion using NaCl solution dilution by pH 9.0 water

| Emulsion Constituents | Stock Emulsion | | | |
|---|---|---|---|---|
| | E30 | E31 | E32 | E33 |
| Clove Oil neat | 5 ml | 5 ml | 5 ml | 5 ml |
| Tween ® 20 (2%) | 100 µl | 100 µl | 100 µl | 100 µl |
| Saffola oil 0.1% | 5 µl | 5 µl | 5 µl | 5 µl |
| NaCl sol'n (10 ppm stock) | 0.1 ppm | 0.05 ppm | 0.02 ppm | 0.01 ppm |

Example 14

Clove oil emulsions E34–E37 were prepared using 0.1 ppm $Na_2HPO_4$ solution by diluting the emulsion with pH 9.0 water instead of adjusting the pH of diluted emulsion (Table 12). These emulsions were tested for their disinfecting activity in 100 ml and 1 L D.W. Disinfection activity of emulsions E34–E37 are shown in Table 13. It was observed that these emulsions with 2% Tween®20, 0.1% Saffola oil, 2 minutes sonication time at each step and 0.1 ppm of $Na_2HPO_4$ at pH 9.0 performed well in disinfection of drinking water, as shown in Table 14.

TABLE 12

Preparation of Clove oil emulsion using $Na_2HPO_4$ solution, dilution by pH 9.0 water

| Emulsion Constituents | Stock Emulsion | | | |
|---|---|---|---|---|
| | E34 | E35 | E36 | E37 |
| Clove Oil Neat | 5 ml | 5 ml | 5 ml | 5 ml |
| Tween ® 20 (2%) | 100 µl | 100 µl | 100 µl | 100 µl |
| Saffola oil | 5 µl | 5 µl | 5 µl | 5 µl |
| $Na_2HPO_4$ sol'n | 0.1 ppm | 0.05 ppm | 0.02 ppm | 0.01 ppm |

Figure 1B:
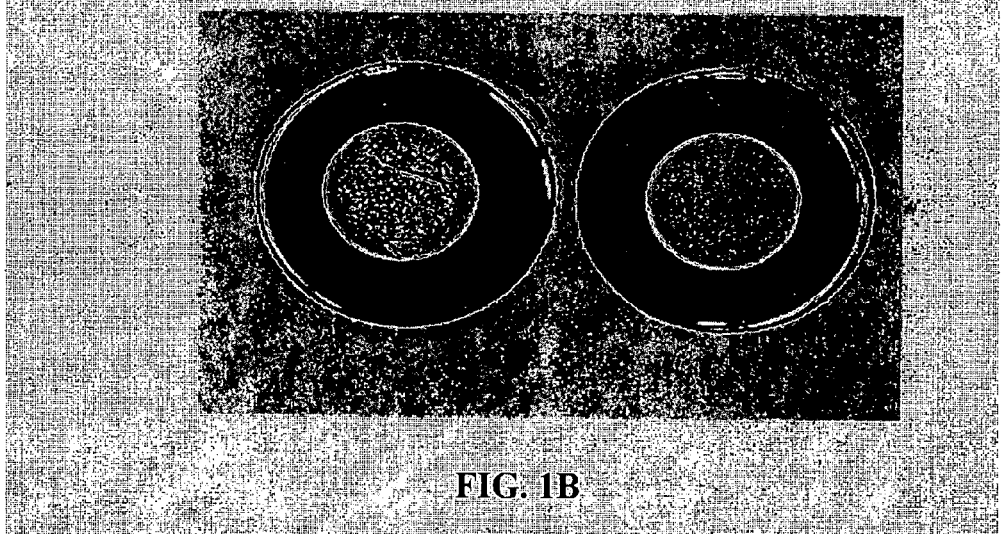
FIG. 1B shows the disinfection activity of a 1:50 dilution of clove oil emulsion E34.

The results in 1:20 and 1:50 dilutions shown that the lower dose of emulsion also reduces the bacterial population to considerable extent and in the safe limits as shown in FIG. 1A (Photograph 7) and FIG. 1B (Photograph 8).

TABLE 13

Disinfection Activity of Clove oil Emulsion on sterile D.W. Inoculated with *E. coli*

| Stock Emulsion No. | Working Diluted emulsions | Inhibitory Effect of Emulsions (Contact time 6 h) Reaction volume | | | | | | | | |
|---|---|---|---|---|---|---|---|---|---|---|
| | | DW 1 ml | | | DW 100 ml | | | DW 1000 ml | | |
| | | 10 µl | 50 µl | 100 µl | 10 µl | 50 µl | 100 µl | 100 µl | 500 µl | 1 ml |
| E1 | 1:10 | − | ++ | ++ | ++ | ++ | − | − | − | |
| | 1:100 | − | ++ | ++ | + | ++ | − | − | − | |
| | 1:500 | − | − | ++ | − | + | − | − | − | |
| | 1:5000 | − | − | − | − | − | − | − | − | |
| E2 | 1:10 | − | ++ | ++ | | | | | | |
| | 1:100 | − | ++ | ++ | | | | − | − | |
| | 1:500 | − | − | ++ | | | | | | |
| E3 | 1:10 | − | ++ | ++ | | | | − | | |
| | 1:100 | − | ++ | ++ | | | | − | − | |
| | 1:500 | − | − | ++ | | | | − | | |
| E4 | 1:10 | − | ++ | ++ | | | | | | |
| | 1:100 | − | ++ | ++ | | | | − | − | |
| | 1:500 | − | − | ++ | | | | | | |
| E5 | 1:10 | ++ | ++ | ++ | | | − | − | − | − |
| | 1:100 | − | ++ | ++ | | | − | | | |
| | 1:500 | − | + | ++ | | | − | | | |
| | 1:5000 | − | − | + | | | | | | |
| E6 | 1:20 | | | | | | + | | | |
| E7 | 1:20 | | | | | | + | | | |
| E8 | 1:20 | | | | | | + | | | |
| E9 | 1:20 | | | | | | + | | | |
| E10 | 1:20 | | | | | | + | | | |
| E11 | 1:20 | − | + | ++ | − | − | − | − | − | − |
| E12 | 1:20 | − | ++ | ++ | − | − | − | − | − | + |
| E13 | 1:20 | | | | − | − | − | − | | |
| E14 | 1:20 | | | | − | − | − | − | | |
| E15 | 1:20 | | | | | | | − | + | |
| E16 | 1:20 | | | | | ++ | | | | |
| E17 | 1:20 | | | | − | ++ | ++ | | | |
| E18 | 1:20 | | | | | ++ | ++ | | | |
| E19 | 1:20 | | | | | ++ | ++ | | | |
| E20 | 1:20 | | | | | ++ | ++ | | | |
| E21 | 1:10 | ++ | ++ | ++ | ++ | ++ | ++ | − | ++ | ++ |
| | 1:50 | ++ | ++ | ++ | + | + | | | | + |
| | 1:100 | + | ++ | ++ | + | + | | | | + |
| | 1:200 | + | + | ++ | − | − | | | | + |
| | 1:500 | − | − | + | − | − | | | | − |

TABLE 13-continued

Disinfection Activity of Clove oil Emulsion on sterile D.W. Inoculated with *E. coli*

| Stock Emulsion No. | Working Diluted emulsions | Inhibitory Effect of Emulsions (Contact time 6 h) Reaction volume | | | | | | | | |
|---|---|---|---|---|---|---|---|---|---|---|
| | | DW 1 ml | | | DW 100 ml | | | DW 1000 ml | | |
| | | 10 μl | 50 μl | 100 μl | 10 μl | 50 μl | 100 μl | 100 μl | 500 μl | 1 ml |
| E22 | 1:10 | ++ | ++ | ++ | | | + | | | + |
| | 1:100 | | | | | | + | | | + |
| E23 | 1:10 | ++ | ++ | ++ | | | + | | | + |
| | 1:100 | | | | | | + | | | + |
| E24 | 1:10 | ++ | ++ | ++ | | | + | | | + |
| | 1:100 | | | | | | + | | | + |
| E25 | 1:10 | ++ | ++ | ++ | | | + | | | + |
| | 1:100 | | | | | | + | | | + |
| E26 | 1:10 | ++ | ++ | ++ | | | ++ | | | + |
| | 1:100 | | | | | | + | | | + |
| E27 | 1:10 | ++ | ++ | ++ | | | ++ | | | + |
| | 1:100 | | | | | | + | | | + |
| E28 | 1:10 | ++ | ++ | ++ | | | ++ | | | + |
| | 1:100 | | | | | | + | | | + |
| E29 | 1:10 | ++ | ++ | ++ | | | ++ | | | + |
| | 1:100 | | | | | | + | | | + |
| E30 | 1:10 | ++ | ++ | ++ | | | + | | | ++ |
| | 1:20 | | | | | | + | | | + |
| | 1:50 | | | | | | + | | | + |
| | 1:100 | | | | | | + | | | + |
| E31 | 1:10 | ++ | ++ | ++ | | | + | | | ++ |
| E32 | 1:10 | ++ | ++ | ++ | | | + | | | + |
| E33 | 1:10 | ++ | ++ | ++ | | | + | | | + |
| E34 | 1:10 | ++ | ++ | ++ | | | ++ | | | ++ |
| | 1:20 | | | | | | + | | | ++ |
| | 1:50 | | | | | | + | | | + |
| | 1:100 | | | | | | + | | | + |
| E35 | 1:10 | ++ | ++ | ++ | | | ++ | | | ++ |
| E36 | 1:10 | ++ | ++ | ++ | | | ++ | | | ++ |
| E37 | 1:10 | ++ | ++ | ++ | | | ++ | | | ++ |

'++' 100% removal,
'+' above 60% removal,
'−' no effect

TABLE 14

Percentage removal of *E. coli* in 100 ml and 1L D.W. by Indicated Clove oil emulsions

| Stock Emulsions | Working Dilutions | % Removal of *E. coli* | |
|---|---|---|---|
| | | (100 μl dose) | (1 ml dose) |
| E22 | 1:10 | 96 | 92 |
| E23 | 1:10 | 98 | 90 |
| E24 | 1:10 | 95 | 89 |
| E25 | 1:10 | 99 | 89 |
| E26 | 1:10 | 100 | 92 |
| E27 | 1:10 | 100 | 94 |
| E28 | 1:10 | 100 | 95 |
| E29 | 1:10 | 100 | 96 |
| E30 | 1:10 | 100 | 100 |
| E31 | 1:10 | 100 | 98 |
| E32 | 1:10 | 97 | 97 |
| E33 | 1:10 | 95 | 97 |
| E34 | 1:10 | 100 | 100 |
| | 1:20 | | 94 |
| | 1:50 | | 91 |
| E35 | 1:10 | 100 | 100 |
| E36 | 1:10 | 100 | 100 |
| E37 | 1:10 | 100 | 100 |

Example 15

After getting 100% inhibition of *E. coli* with 1:10 emulsion in spiked 1 L water 1:20, 1:30, 1:40 and 1:50 oil-in-water emulsions of clove oil were prepared. The emulsions when tested in 1 L spiked water at the fixed dose of 1 ml showed complete inhibition of $10^5$ and $10^3$ *E. coli* after 6 hrs contact period with 1:20 emulsion. 1:30, 1:4,1:50 emulsions also showed appreciable inhibition as shown in Table 15.

The result in 1:50 dilution shows that the lower dose of emulsion also reduces the bacterial population to considerable extent.

| Emulsion (Oil:Water) | Percentage Inhibition of *E. coli* |
|---|---|
| 1:10 | 100 |
| 1:20 | 100 |
| 1:30 | 96 |
| 1:40 | 95 |
| 1:50 | 91 |

Example 16

Well Water Experiments

Well water experiments were performed in 1 L-water samples from various areas of Nagpur City, India. The well water samples were in use for household purposes. Control as well as test samples were given 6 hrs and overnight contact period with a standardized dose of 1 ml of 1:10 dilution of clove oil emulsion. After the specific contact period, 25 ml of the aliquot was filtered through sterile 0.45 μm size membrane filters. The filters were placed on MEC media and incubated at 44.5° C. overnight as described in the general methods above. The membranes were treated with the urea solution and the yellow colonies counted in control as well as experimental samples. The results are shown below in Table 16.

TABLE 16

| Area | % Removal 6 hrs contact period | % Removal Overnight contact period | Colony Characteristics |
|---|---|---|---|
| Ramdaspeth | 70 | 80 | Blue |
| Bharatnagar | 40 | 75 | Bright yellow |
| Mankapur | 70 | 90 | Yellow blue |
| Samarthnagar | 75 | 90 | Yellow blue |
| Bazargaon/Murli | 50 | 65 | Dark blue |
| Dharampeth | 50 | 80 | Dirty yellow |
| Kachipura | 70 | 90 | Yellow blue |
| Snehnagar | 50 | 70 | Yellow blue |

All references discussed herein are incorporated by reference. One skilled in the art would readily appreciate the present invention is well adapted to carry out the stated objects and obtain the disclosed ends and advantages, as well as those inherent herein. The present invention may be embodied in other specific forms without departing from the spirit or essential attributes thereof. Therefore, any descriptions of specific embodiments in the foregoing disclosure is not to be construed as limiting the scope of the present invention.

We claim:

1. A composition for disinfecting pathogenic micro-organisms present in water enabling the water to be potable, comprising:

(a) an emulsifier;

(b) an essential oil of Kapur Tulsi (*Ocimum kilimandscharicum*); and (c) optionally an electrolyte and optionally a carrier oil comprising a plant oil.

2. The composition as claimed in claim 1, wherein the essential oil further comprises clove oil or eucalyptus oil.

3. The composition as claimed in claim 1, wherein the emulsifier comprises a polysorbate surfactant.

4. The composition as claimed in claim 1, wherein the emulsifier is selected from the group consisting of poloxamers, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, and emulsifying wax.

5. The composition as claimed in claim 4, wherein the emulsifier comprises polysorbate 20.

6. The composition as claimed in claim 1, wherein the emulsifier is present in the composition in a range of about 0.5 to 4.0 wt. % of total essential oil.

7. The composition as claimed in claim 6, wherein the emulsifier is present in the composition in a range of about 1.5 to 3.0 wt. % of total essential oil.

8. The composition as claimed in claim 1, wherein the carrier oil comprises an unsaturated vegetable oil.

9. The composition as claimed in claim 1, wherein the carrier oil is present in the composition in a range of about 0.01 to 5.0 wt. % of total essential oil.

10. The composition as claimed in claim 9, wherein the carrier oil is present in the composition in a range of about 0.01 to 0.5 wt % of total essential oil.

11. The composition as claimed in claim 1, wherein the electrolyte is sodium chloride (NaCl) or disodium hydrogen phosphate ($Na_2HPO_4$).

12. The composition as claimed in claim 1, wherein the electrolyte is present in the composition in a range of about 0.01 to 0.1 ppm of essential oil.

* * * * *